(12) United States Patent
Fares et al.

(10) Patent No.: US 8,617,578 B2
(45) Date of Patent: Dec. 31, 2013

(54) COMPOSITIONS CONTAINING TOPICAL-ACTIVE AGENTS AND PENTYLENEGLYCOL

(75) Inventors: Hani Fares, Somerset, NJ (US); Marc Cornell, Jackson, NJ (US); Peter Foltis, Nutley, NJ (US); Isabelle Hansenne, Westfield, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/417,859

(22) Filed: Mar. 12, 2012

(65) Prior Publication Data

US 2012/0196843 A1 Aug. 2, 2012

Related U.S. Application Data

(63) Continuation of application No. 11/194,319, filed on Aug. 1, 2005, now abandoned, which is a continuation-in-part of application No. 10/646,300, filed on Aug. 22, 2003, now abandoned.

(51) Int. Cl.
| | |
|---|---|
| *A61K 8/63* | (2006.01) |
| *A61Q 19/00* | (2006.01) |
| *A61K 9/00* | (2006.01) |
| *A61P 29/00* | (2006.01) |
| *A61K 8/34* | (2006.01) |

(52) U.S. Cl.
USPC .............................. 424/401; 424/62; 424/400

(58) Field of Classification Search
USPC ........................................... 424/401, 62, 400
See application file for complete search history.

(56) References Cited

U.S. PATENT DOCUMENTS

| | | | |
|---|---|---|---|
| 2,880,130 A | 3/1959 | Johnson | |
| 3,899,580 A | 8/1975 | O'Neill et al. | |
| 4,289,764 A | 9/1981 | Yarrow et al. | |
| 4,305,936 A | 12/1981 | Klein | |
| 4,383,992 A | 5/1983 | Lipari | |
| 4,552,872 A | 11/1985 | Cooper et al. | |
| 4,778,060 A | 10/1988 | Wessner, Jr. | |
| 4,853,379 A | 8/1989 | Shroot et al. | |
| 4,971,789 A | 11/1990 | Vanlerberghe et al. | |
| 5,174,995 A | 12/1992 | Davis | |
| 5,190,936 A | 3/1993 | Laugier et al. | |
| 5,229,370 A | 7/1993 | Ammeraal | |
| 5,275,755 A | 1/1994 | Sebag et al. | |
| 5,607,980 A | 3/1997 | McAtee et al. | |
| 5,643,898 A | 7/1997 | Grollier et al. | |
| 5,660,839 A | 8/1997 | Allec et al. | |
| 5,679,374 A | 10/1997 | Fanchon et al. | |
| 5,688,514 A | 11/1997 | Chaudhry et al. | |
| 6,075,056 A | 6/2000 | Quigley, Jr. et al. | |
| 6,113,888 A | 9/2000 | Castro et al. | |
| 6,197,287 B1 | 3/2001 | Mallo et al. | |
| 6,245,821 B1 | 6/2001 | Bulcourt et al. | |
| 6,274,124 B1 | 8/2001 | Vollhardt | |
| 6,299,900 B1 | 10/2001 | Reed et al. | |
| 6,346,239 B1 | 2/2002 | Mallo et al. | |
| 6,372,204 B1 | 4/2002 | Michel-Lecocu et al. | |
| 6,375,959 B1 | 4/2002 | Mallo et al. | |
| 6,531,561 B2 | 3/2003 | Candau et al. | |
| 6,673,861 B2 | 1/2004 | Tabacchi et al. | |
| 6,833,419 B2 | 12/2004 | Morschhauser et al. | |
| 6,905,674 B2 | 6/2005 | L'Alloret | |
| 2001/0051686 A1 | 12/2001 | Tabacchi et al. | |
| 2001/0053801 A1 | 12/2001 | Tabacchi et al. | |
| 2003/0027864 A1 | 2/2003 | Guiramand et al. | |
| 2003/0072732 A1 | 4/2003 | Breton et al. | |
| 2004/0096406 A1 | 5/2004 | De Poilly | |
| 2005/0022977 A1 | 2/2005 | Kohara et al. | |
| 2005/0043283 A1 | 2/2005 | Fares et al. | |

FOREIGN PATENT DOCUMENTS

| | | |
|---|---|---|
| EP | 0 321 951 A | 6/1989 |
| EP | 1 078 636 A1 | 2/2001 |
| GB | 2 131 693 A | 6/1984 |
| JP | 2002-87926 | 3/2002 |
| WO | WO 96/20712 A1 | 7/1996 |
| WO | WO 99/33471 A1 | 7/1999 |
| WO | WO 03/011244 A1 | 2/2003 |
| WO | WO 2005/004830 A | 1/2005 |

OTHER PUBLICATIONS

Seppic, SEPIGEL™ 305, p. 1-38, Jun. 2004.
Seppic, SEPIPLUS™ 400, SEPIPLUSa 265, p. 1-41, Nov. 2004.
Seppic, SIMULGEL™ E6, p. 1-39, Dec. 2001.
Seppic, SIMULGEL™ 600, p. 1-14, Dec. 2001.
Noveon, AMPS® Monomer, http://www.noveon.com/products/amps/, p. 1-3, Jun. 2, 2005.
Noveon, AMPS® Monomer, http://www.noveon.com/products/amps/products.asp, p. 1-3, Jun. 2, 2005.

*Primary Examiner* — Rachael E Bredefeld
(74) *Attorney, Agent, or Firm* — Novak Druce Connolly Bove + Quigg LLP

(57) ABSTRACT

Disclosed are cosmetic and dermatological compositions containing hydrocortisone or a derivative thereof, a glycol and a thickening or gelling agent, and methods of making and using them.

16 Claims, No Drawings

COMPOSITIONS CONTAINING TOPICAL-ACTIVE AGENTS AND PENTYLENEGLYCOL

CROSS-REFERENCE TO RELATED APPLICATIONS

This application is a continuation of U.S. patent application Ser. No. 11/194,319, filed Aug. 1, 2005, which is a continuation-in-part of U.S. patent application Ser. No. 10/646,300, filed Aug. 22, 2003, and now abandoned, the disclosures of which are incorporated herein by reference.

BACKGROUND OF THE INVENTION

Hydrocortisone is used in many topical preparations as a treatment for temporary relief of itching associated with minor skin irritation, inflammation and rashes due to eczema, insect bites, poison ivy, poison oak, poison sumac, soaps, detergents, cosmetics, seborrheic dermatitis, psoriasis and itching in the genital and anal areas of the body. Hydrocortisone has limited solubility in water. Thus, it is necessary to add co-solvents, surfactants, and/or complexing agents to obtain an aqueous solution of hydrocortisone in sufficient concentration to be therapeutically efficacious.

U.S. Pat. No. 2,880,130 discloses the use of polyoxyethylene sorbitan monooleate (Tween 80®) in amounts of from 2-25 percent of the vehicle to obtain clear aqueous solutions containing up to 0.2% of hydrocortisone. U.S. Pat. No. 4,289,764 describes formulations containing 0.025 to 0.4% hydrocortisone in an aqueous solution of 15-50% propylene glycol that is acidified to pH 2.7-3.3 with a non-toxic organic acid such as citric acid. U.S. Pat. No. 4,305,936 provides for a 0.005-2.5% hydrocortisone clear liquid formulation containing 1-4% by weight of a glyceryl ester of fatty acids having 6-22 carbon atoms, 1-3% by weight of the hydrocortisone of a betaine surfactant, and 10-50% of an alkanol co-solvent, preferably ethanol. U.S. Pat. No. 4,778,060 describes a 0.5% hydrocortisone aqueous solution for use as a douche and for impregnating towelettes for wipes. The solution also contains caprylic/capric triglycerides (5-20%), sorbitan stearate (2-4%), Polysorbate 60® (1-3%), preservatives and citric acid.

U.S. Pat. No. 4,383,992 discloses an aqueous solution of an inclusion complex of unbranched beta-cyclodextrin and hydrocortisone and reveals that the inclusion complex must dissociate before the hydrocortisone is physiologically active. U.S. Pat. No. 5,229,370 discloses an aqueous solution on an inclusion complex composed of a branched beta-cyclodextrin and hydrocortisone. U.S. Pat. No. 4,853,379 teaches hydrocortisone compositions containing a mixture of solvents which are an aliphatic alcohol, propylene glycol and dimethyl coco-benzylammoniurn chloride. U.S. Pat. No. 4,971,789 teaches various ionic polyethers as solubilizers for pharmaceuticals such as hydrocortisone. U.S. Pat. No. 5,190,936 teaches compositions containing hydrocortisone and a lipid phase of nonionic amphiphilic lipid vesicles. GB 2,131,693 teaches hydrocortisone compositions containing a solvent mixture of (i) a caprolactam and (ii) 2-isostearyl-1-hyroxylethyl-1-benzylimidazolinium chloride or an alkylphenol polyglycerol. WO 96/20712 teaches aqueous solutions of hydrocortisone free of lower alcohols that contain sodium dioctyl sulfosuccinate in mixtures of glycerin, propylene glycol and polyethylene glycol.

SUMMARY OF THE INVENTION

A first aspect of the present invention is directed to a cosmetic composition for application to skin or scalp, comprising: hydrocortisone or a derivative thereof; at least one glycol; and a thickening or gelling agent comprising a polymeric constituent, an aqueous phase, at least one emulsifier, and optionally an oil phase comprising a hydrocarbon, wherein the polymeric constituent is selected from the group consisting of:

A) an polyelectrolyte that is a homopolymer based on a monomer having a partially or completely salified strong acid functional group, or a copolymer based on at least one monomer having a partially or completely salified strong acid functional group copolymerized with acrylamide;

B) an anionic polyelectrolyte based on at least one monomer possessing a strongly acidic function, copolymerized either with at least one monomer possessing a weakly acidic function or with at least one neutral monomer;

C) a homopolymer of acrylamide or a copolymer containing units derived from (a) acrylamide (b) AMPS, and (c) a polyfunctional monomer in an amount of from 0.12 to 2 milliequivalents inclusive per mole of total monomer units, at least some of the AMPS units being in a neutral salt form;

D) an anionic polyelectrolyte based on partially neutralized acrylic acid; and

E) at least one anionic polyelectrolyte chosen from: branched or crosslinked homopolymers of a monomer possessing a (i) partially or completely salified strong acid functional group, (ii) branched or crosslinked homopolymers of a monomer possessing a partially or completely salified weak acid functional group, (iii) branched or crosslinked copolymers of monomers possessing a partially or completely salified strong acid functional group, (iv) branched or crosslinked copolymers of monomers possessing a partially or completely salified weak acid functional group, (v) branched or crosslinked copolymers of monomers possessing a partially or completely salified strong acid functional group and either of at least one monomer possessing a partially or completely salified weak acid functional group and/or of at least one neutral monomer, and (vi) branched or crosslinked copolymers of monomers possessing a partially or completely salified weak acid functional group and at least one neutral monomer. The thickening or gelling agents containing the polymeric constuents corresponding to subparagraphs A)-E) are referred to herein as first, second, third, fourth and fifth embodiments respectively.

A second aspect of the present invention is directed to method of increasing stability of hydrocortisone or a derivative thereof, comprising: combining hydrocortisone or a derivative thereof; at least one glycol; and the forementioned thickening or gelling agent; thereby preparing a cosmetic composition for application to skin or scalp.

A third aspect of the present invention is directed to a method of treating skin or scalp, comprising applying to skin a cosmetic composition comprising: hydrocortisone or a derivative thereof; at least one glycol; and the forementioned thickening or gelling agent.

The compositions of the present invention may be formulated in a variety of ways, e.g., as a gel, emulsion, ointment, shampoo or lotion. They may be applied to skin or scalp for cosmetic or dermatological purposes e.g., for conditions amenable to treatment with hydrocortisone and derivatives thereof.

Compositions of the present invention are relatively stable from the standpoints of chemical stability of hydrocortisone and cosmetic aesthetics.

DETAILED DESCRIPTION OF THE INVENTION

The thickening/gelling agents useful in the present invention are emulsions that contain a polymeric constituent, at least one emulsifier comprising an oil-in-water (O/W) and/or a water-in-oil (W/O) emulsifier, and optionally an oil phase containing a hydrocarbon and an aqueous phase.

As used herein, the term "emulsifying agent of the water-in-oil type" refers to emulsifying agents having an HLB value that is sufficiently low to provide water-in-oil emulsions, such as the surface-active polymers (e.g., polyethylene glycol poly (hydroxystearic acid) block copolymer, or such as sorbitan esters, for example the sorbitan monooleate sold by Seppic under the tradename of Montane™ 80 or the sorbitan isostearate sold by Seppic under the tradename of Montane™ 70. These emulsifying agents can also include the sorbitan oleate ethoxylated with 5 mol of ethylene oxide sold by Seppic under the tradename of Montanox™ 81, the diethoxylated (2 EO) marketed by Seppic under the name SIMULSOL™ OC72, or the sorbitan sesquioleate marketed by Seppic under the name MONTANE™ 83.

As used herein, the term "emulsifying agent of the oil-in-water type" refers to emulsifying agents having an HLB value that is sufficiently high to provide oil-in-water emulsions, such as ethoxylated sorbitan esters, for example the sorbitan oleate ethoxylated with 20 mol of ethylene oxide sold by Seppic under the name of Montanox™ 80, the ethoxylated castor oil comprising 40 mol of ethylene oxide sold by Seppic under the name of Simulsol™ OL 50, the ethoxylated sorbitan laurate comprising 20 mol of ethylene oxide sold by Seppic under the name of Moneanox™ 20 or the ethoxylated lauryl alcohol comprising 7 mol of ethylene oxide sold by Seppic under the name of Simulsol™ P7, and by Cognis under the tradename Mergital LT7. Other O/W emulsifiers are commercially available from Uniqema under the tradenames Polysorbate 80 and Polysorbate 20.

Other examples of emulsifying agents having an HLB value that is sufficiently high to provide oil-in-water emulsions include the compounds of formula (I):

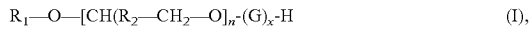

$$R_1—O—[CH(R_2—CH_2—O]_n-(G)_x-H \qquad (I),$$

in which $R_1$ represents a saturated or unsaturated and linear or branched hydrocarbonaceous radical comprising from 1 to 30 carbon atoms, $R_2$ represents a hydrogen atom or an alkyl radical comprising 1 or 2 carbon atoms, G represents the residue of a saccharide, x represents a decimal number between 1 and 5 and n is equal either to zero or to an integer between 1 and 30.

The term "residue of a saccharide" denotes, for G, a bivalent radical resulting from the removal on a sugar molecule, on the one hand, of a hydrogen atom of a hydroxyl group and, on the other hand, of the anomeric hydroxyl group. The term "saccharide" denotes in particular glucose or dextrose, fructose, mannose, galactose, altrose, idose, arabinose, xylose, ribose, gulose, lyxose, maltose, maltotriose, lactose, cellobiose, dextran, talose, allose, raffinose, laevoglucan, cellulose or starch. The oligomeric structure (G) can exist under any form of isomerism, whether optical isomerism, geometrical isomerism or positional isomerism. It can also represent a mixture of isomers.

In formula (I), the radical:

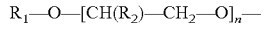

$$R_1—O—[CH(R_2)—CH_2—O]_n—$$

is bonded to G via the anomeric carbon, so as to form an acetal functional group. The divalent group —[CH(R$_2$)—CH$_2$—O]$_n$— represents either a chain composed solely of ethoxyl groups (R$_2$=H) or a chain composed solely of propoxyl groups (R$_2$=CH$_3$) or a chain composed both of ethoxyl groups and of propoxyl groups. In the latter case, the fragments —CH$_2$—CH$_2$—O— and —CH(CH$_3$)—CH$_2$—O— are distributed in the chain in a block or random fashion.

The number x represents the mean degree of polymerization of the saccharide, is generally from 1 to 3, preferably from 1.05 to 2.5, more preferably from 1.1 to 2.0 and most preferably less than or equal to 1.5.

Emulsifying surface-active agents having an HLB value that is sufficiently high to provide oil-in-water emulsions include more particularly the compounds of formula (I) in which G represents the glucose residue or the xylose residue and/or in which n is equal to 0 and/or in which $R_1$ represents a radical comprising from 8 to 18 carbon atoms and more particularly in which $R_1$ represents a radical chosen from the octyl, decyl, undecyl, dodecyl, tetradecyl or hexadecyl radicals, the said radicals being linear or branched.

The oil phase contains a hydrocarbon, which is generally a commercial mineral oil containing saturated hydrocarbons such as paraffins, isoparaffins and cycloparaffins, having, at room temperature, a density of between 0.7 and 0.9, such as for example ISOPAR™ G, ISOPAR™ H, ISOPAR™ I, ISOPAR™ J, ISOPAR™ L, ISOPAR™ M, EXXOL™ D 100 S or MARCOL™ 52 marketed by EXXON CHEMICAL, squalane, hydrogenated polyisobutene, isohexadecane or isododecane, either a synthetic oil, a plant oil, or a mixture of several of these oils. Isohexadecane, which is identified in Chemical Abstracts by the number RN=93685-80-4, is a mixture of $C_{12}$, $C_{16}$ and $C_{20}$ isoparaffins comprising at least 97% of $C_{16}$ isoparaffins, among which the main constituent is 2,2,4,4,6,8,8-heptamethylnonane (RN=4390-04-9). It is sold in France by Bayer. Isododecane is sold in France by Bayer. Hydrogenated polyisobutene is supplied by BP under the trade name of Panalane L-14E. Squalane is identified in Chemical Abstracts by the number RN=111-01-3, and is generally known to be a mixture of hydrocarbons comprising more than 80% by weight of 2,6,10,15,19,23-hexamethyltetracosane. As used herein, the term "white mineral oil" refers to a white mineral oil in accordance with the FDA regulations 21 CFR 172.878 and FR 178.3620(a). An example is Marcol™52, which is a commercial oil corresponding to the definition of liquid paraffins of the French Pharmacopoeia. Other mineral oils suitable for use in the present invention are available commercially from Exxon Mobil, e.g., under the trade name Primol 352, and from Pencreco, e.g., Drakeol 13.

In the first, second, third and fourth embodiments, the oil phase, if present, generally constitutes about 15% to about 40%, preferably about 20% to about 25%, of the total weight of the thickening/gelling agent. In the fifth embodiments, the oil phase, if present, constitutes no more than about 19%, and in some cases, no more than about 5% by weight of the gelling agent.

In various first embodiments, the thickening/gelling agent contains at least one emulsifying agent of water-in-oil (W/O) type and/or at least one emulsifying agent of oil-in-water (O/W) type in the form of a self-invertible inverse latex containing from about 20% to about 70% by weight and preferably from about 25% to about 50% by weight of a polyelectrolyte that may be branched or crosslinked. The polyelectrolyte is either a homopolymer based on a monomer having a partially or completely salified strong acid functional group, or a copolymer based on at least one monomer having a partially or completely salified strong acid functional group copolymerized with acrylamide.

The term "crosslinked polymer", as used herein, (i.e., in this specification), refers to a non-linear polymer that exists in the state of a three-dimensional network which is insoluble in water but is swellable in water and which thus results in the production of a chemical gel. The term "branched polymer", as used herein, refers to a non-linear polymer that has pendant chains so as to obtain, when this polymer is dissolved in water, a high degree of entangling leading to very high low-gradient viscosities. The composition can contain crosslinked units and/or branched units. Crosslinking agents and/or the branching agents include diethylenes and polyethylenes e.g., diallyloxyacetic acid or one of its salts, such as sodium diallyoxyacetate, ethylene glycol dimethacrylate, ethylene glycol diacrylate, diallylurea, trimethylolpropane triacrylate, methylenebis(acrylamide), triallylamine, and mixtures thereof.

The strong acid functional group of the monomer is preferably a sulphonic acid functional group or a phosphonic acid functional group, partially or completely salified. The monomer can be, for example, partially or completely salified styrenesulphonic acid, preferably 2-methyl-2-[(1-oxo-2-propenyl)amino]-1-propanesulphonic acid (AMPS™, commercially available from the Lubrizol Corp.), partially or completely salified in the form of an alkali metal salt, e.g., the sodium salt ("AMPS Na"), the potassium salt, the ammonium salt or a salt of an aminoalcohol, e.g., the monoethanolamine salt.

In some of these first embodiments, the polyelectrolyte is a copolymer containing in molar proportions, from about 30% to about 50% of 2-methyl-2-[(1-oxo-2-propenyl)amino]-1-propanesulphonic acid (AMPS™), partially or completely salified in the form of the sodium salt or of the ammonium salt, and from about 50% to about 70% of acrylamide.

In some other first embodiments, the polyelectrolyte is a homopolymer of 2-methyl-2-[(1-oxo-2-propenyl)amino]-1-propanesulphonic acid (AMPS™) partially or completely salified in the form of the sodium salt or of the ammonium salt.

In yet other first embodiments, the polyelectrolyte is crosslinked and/or branched with a diethylenic or polyethylenic compound, preferably triallylamine, in the molar proportion, expressed with respect to the monomers employed, of about 0.005% to about 1%, more preferably of about 0.01% to about 0.5% and most preferably of about 0.1% to about 0.25%.

In these first embodiments, the inverse latex as defined above generally comprises from about 4% to about 10% by weight of emulsifying agents. In embodiments containing both types of emulsifiers, about 20% to about 50% and preferably about 25% to about 40% of the total weight of the emulsifiers are of the water-in-oil type, and about 80% to about 50% and preferably from about 75 to about 60% are of the oil-in-water type.

Methods of making these agents are disclosed in U.S. Pat. No. 6,673,861. In preferred embodiments, the thickening/gelling agent comprises a homopolymer of AMPS, isohexadecane and Polysorbate 80, commercially available from SEPPIC under the tradename Simulgel 800 (INCI name: Sodium Polyacryloyldimethyl taurate and Isohexadecane and Sorbitan Oleate). In other preferred embodiments, the thickening/gelling agent comprises a copolymer of AMPS Na and acrylamide, isohexadecane and Polysorbate 80, commercially available from SEPPIC under the tradename Simulgel 600 (INCI name: Acrylamide and sodium acryloyldimethyl taurate copolymer and Polysorbate 80).

In various second embodiments, the thickening/gelling agent contains at least one emulsifier of water-in-oil (W/O) type and/or at least one emulsifier of oil-in-water (O/W) type, and is in the form of an inverted latex containing from about 20% to about 60% by weight, and preferably from about 25% to about 45% by weight, of a branched or crosslinked anionic polyelectrolyte based on at least one monomer possessing a strongly acidic function, copolymerized either with at least one monomer possessing a weakly acidic function or with at least one neutral monomer.

In some of these second embodiments, the anionic polyelectrolyte is the result of a copolymerization of its precursor monomers, which is carried out at a pH below 4. In other embodiments, about 30% to about 90% of the monomer units that contain the anionic polyelectrolyte have a strongly acidic function.

The strongly acidic function of the monomer containing it is preferably a sulphonic acid function or a phosphonic acid function, partially or totally salified. The monomer can be for instance, styrenesulfonic acid partially or totally salified, preferably 2-methyl-2-[(1-oxo-2-propenynamino]-1-propanesulphonic acid (AMPS) partially or totally salified in the form of an alkali metal salt (e.g., "AMPS Na") or an ammonium salt. The weakly acidic function of the monomer containing it is, in particular, a carboxylic acid function, and the monomer is preferably chosen from acrylic acid, methacrylic acid, itaconic acid and maleic acid. The neutral monomer is chosen in particular from 2-hydroxyethyl acrylate, 2,3-dihydroxypropyl acrylate, 2-hydroxyethyl methacrylate and 2,3-dihydroxypropyl methacrylate, or an ethoxylated derivative, with a molecular weight between about 400 and about 1000, of each of these esters.

In some of these second embodiments, the reverse latex contains from about 20% to about 60% by weight, and preferably from about 25% to about 45% by weight, of a branched or crosslinked, anionic polyelectrolyte based on partially or totally salified 2-methyl-2-[(1-oxo-2-propenyl)amino]-1-propanesulfonic acid (AMPS), copolymerized with 2-hydroxyethyl acrylate, more particularly, a composition as defined above, characterized in that about 30% to about 90%, preferably about 50% to about 90%, in molar proportions, of the monomer units comprised by the anionic polyelectrolyte is 2-methyl-2-[(1-oxo-2-propenyl)amino]-1-propanesulfonic acid (AMPS) partially or totally salified, and in particular a composition as defined above, for which the anionic polyelectrolyte contains, in molar proportions, from about 60% to about 90% of sodium salt or of ammonium salt of 2-methyl-2[(1-oxo-2-propenyl)amino]-1-propanesulfonic acid and from about 10% to about 40% of 2-hydroxyethyl acrylate.

In some other second embodiments, the reverse latex contains from 20% to 60% by weight, and preferably from about 30% to about 45% by weight, of a branched or crosslinked, anionic polyelectrolyte based on AMPS, which is partially or totally salified in the form of sodium salt (e.g., AMPS Na) or of ammonium salt, copolymerized with acrylic acid, partially salified in the form of the sodium salt or of ammonium salt.

In some other second embodiments, the anionic polyelectrolyte is crosslinked and/or branched with a diethylenic or polyethylenic compound in a molar proportion, expressed relative to the monomers used, of about 0.005% to about 1% and preferably about 0.01% to about 0.2%, and more particularly about 0.01% to about 0.1%, and preferably that for which the crosslinking agent and/or the branching agent is chosen from ethylene glycol dimethacrylate, sodium diallyloxyacetate, ethylene glycol diacrylate, diallylurea, trimethylolpropane triacrylate or methylene-bisacrylamide.

In these second embodiments, the reverse latex generally contains about 2.5% to about 15% by weight, and preferably about 4% to about 9% by weight, of emulsifiers. In embodiments that contain both types of emulsifiers, about 20% to about 50%, and preferably about 25% to about 40% of the total weight of the emulsifiers present are of the water-in-oil (W/O) type, and in which about 80% to about 50%, in particular about 75% to about 60%, of the total weight of the emulsifiers are of the oil-in-water (O/W) type.

In preferred second embodiments, the oil phase contains Marcol™ 52 or isohexadecane.

Methods for making these thickening/gelling agents are disclosed in U.S. Pat. No. 6,197,287. A suitable process entails the following:

a) an aqueous solution containing the monomers and the optional additives is emulsified in an oil phase in the presence of one or more emulsifiers of water-in-oil type;

b) the polymerization reaction is initiated by introducing a free-radical initiator into the emulsion formed in a), after which the reaction is left to proceed; and c) when the polymerization reaction is complete, one or more emulsifiers of oil-in-water type are introduced at a temperature below 50° C.

According to a variant of this process, the reaction medium obtained after step b) is concentrated by distillation before step c) is carried out. In a preferred embodiment, the polymerization reaction is initiated by a redox couple, such as the cumene hydroperoxide/sodium metabisulphite couple, at a temperature below or equal to 10° C., and is then carried out either in a virtually adiabatic manner up to a temperature above or equal to 40° C., more particularly above or equal to 50° C., or by controlling the temperature evolution. In another preferred embodiment, the starting aqueous solution is adjusted to a pH below or equal to 4 before step c) is carried out.

In preferred embodiments, the branched or crosslinked, anionic polyelectrolyte is based on AMPS, which is partially or totally salified in the form of sodium salt, copolymerized with acrylic acid, partially salified in the form of the sodium salt; the emulsifier comprises Polysorbate 80, and the oil phase contains isohexadecane. It is commercially available from SEPPIC under the tradename Simulgel EG (INCI name: sodium acrylate and acryloyldimethyl taurate copolymer and isohexadecane and Polysorbate 80).

In some third embodiments, the thickening/gelling agent is in the form of a water-in-oil (W/O) emulsion containing polymeric material, in which at least 98% of the polymeric material in the emulsion is water soluble, and the polymeric material comprises polyacrylamide or units derived from (a) acrylamide (b) AMPS, and (c) a polyfunctional monomer in an amount of from 0.12 to 2 milliequivalents inclusive per mole of total monomer units, wherein AMPS is partially or completely salified (in a neutral salt form), e.g., AMPS Na, such that the aqueous phase of the water in oil emulsion has a pH of at least 5.5.

The water-in-oil emulsion of the polymer can be obtained by the inverse emulsion polymerization reaction of the neutralized salt of AMPS with acrylamide. They are reacted simultaneously with a small amount of the crosslinking agent to produce a partially crosslinked structure which is still water soluble. As the copolymers are derived from anionic and nonionic monomers they are compatible, and hence effective, in formulated systems of either anionic or nonionic character.

Methods of making these agents and other polymers useful in these embodiments are disclosed in U.S. Pat. No. 5,688,514 (and references therein). As disclosed in the '514 patent, these polymers remain dissolved in the aqueous phase of the inverse emulsion, both during and after polymerization. In addition, the following conditions apply.

1) The crosslinking monomer must contain 2 or more sites of unsaturation and be sufficiently water soluble to react with aqueous acrylamide and neutralized or partially neutralized AMPS™ monomers to produce a partially crosslinked copolymer that is still water soluble. The water solubility of the crosslinking agent is preferably at least 1% by weight of solution. Preferred crosslinking agents are allyl sucrose, allyl pentaerythritol, and MBA. To retain solubility and to achieve optimum thickener/stabilizer efficiency, the molar ratio of crosslinking agent to the monomer mixture is critical; for MBA good results may be achieved within the range about 0.06 to about 1, preferably about 0.08 to about 0.7, the optimum being between about 0.1 and about 0.4 m·moles/mole, inclusive, of the monomer mixture. The precise quantity of crosslinking agent may be selected in dependence upon the proportion of AMPS in the monomer mix, larger proportions of AMPS possibly requiring slightly larger proportions of crosslinking agent.

2) The ratio, expressed as mole %, between the main monomers in the copolymer composition namely acrylamide/neutralized AMPS may be between 85/15 and 15/85, preferably between 70/30 and 30/70, more preferably between 65/35 and 35/65, especially between 60/40 and 40/60, inclusive.

3) Preferred neutralizing agents for AMPS are sodium or potassium hydroxide or water soluble/miscible amines of low toxicity (e.g., triethanolamine) or mixtures thereof.

4) Polymerization may be carried out at a pH≥5.5, preferably ≥6.0 and most preferably ≥6.5, but ≤10.0.

5) Oil in water emulsifiers or mixtures of emulsifiers, having an individual or composite HLB value≥10, preferably ≥11 and most preferably ≥12 and other additives such as inverse emulsion stabilizers, wetting agents, anti foams or combinations or mixtures thereof may be added to the water-in-oil emulsion. In an especially preferred process, an inverse monomer emulsion is formed before polymerization, in which case the oil in water emulsifier and other additives are added after the emulsification of the disperse and continuous phases. However, they then may be added at any time before, during or after the polymerization process. Preferably, at least some, more preferably all, of the oil in water emulsifier is added after the polymerization process.

6) The polymer solids content of the water-in-oil emulsion is preferably 35-60%, more preferably 40-50% by weight of the total weight of the emulsion.

Compositions may be prepared by incorporating the water in oil emulsion into the remaining components, whereupon the emulsion "inverts" to provide a continuous liquid phase comprising the aqueous medium of the emulsion and any liquid in the composition comprising water or miscible with water. Preferably, essentially all of the polymer is dissolved in the liquid phase. Topically acceptable adjuvants such as the liquid carrier, for example, an alcohol and/or glycol, optionally mixed with water, will then form part of the continuous liquid phase, other topically acceptable adjuvants which are insoluble or only partially soluble in the liquid phase being present in suspension or emulsion.

Preferred third embodiments include polyacrylamide or acrylamide/AMPS Na, isoparaffin and Laureth-7. Such a product is commercially available from Seppic (France) under the tradename Sepigel 305 (INCI name: Polyacrylamide and C13-C-14 isoparaffin and Laureth-7).

In fourth embodiments, the thickening/gelling agent contains at least one emulsifier of water-in-oil (W/O) type and/or at least one emulsifier of oil-in-water (O/W) type, in the form of a reverse latex containing from about 20% to about 70% by weight, and preferably from about 25% to about 40% by weight, of an anionic polyelectrolyte. The anionic polyelectrolyte is based on partially neutralized acrylic acid and may be branched and/or crosslinked.

As used herein, the term "partially neutralized acrylic acid" refers to acrylic acid partially salified in the form of an alkali salt, such as the sodium or potassium salt, or in the form of the salt of a nitrogenous base, such as the ammonium salt, or a salt with a compound containing quaternary ammonium, such as an amino alcohol salt. It is preferably acrylic acid partially neutralized in the form of the ammonium salt ($NH_4$) or a monoethanolamine salt ($HOCH_2CH_2NH_3^+$).

As used herein, the term "amino alcohol" refers to mono- or poly(hydroxyalkyl)amines.

In preferred fourth embodiments, the anionic polyelectrolyte is crosslinked and/or branched. The crosslinking and/or branching agent is generally used in a molar proportion, expressed relative to the monomers used, of about 0.05% to about 0.5% and preferably about 0.1% to about 0.25%.

In these embodiments, the latex generally contains about 2.5% to about 15% by weight and preferably about 4% to about 9% by weight, of emulsifiers. In embodiments containing both W/O and O/W emulsifiers, about 20% to about 50%, in particular about 25% to about 40%, of the total weight of the emulsifiers present are of the water-in-oil (W/O) type and about 80% to about 50%, in particular about 75% to about 60%, of the total weight of the emulsifiers are of the oil-in-water (O/W) type. In preferred embodiments, the emulsifier is an O/W emulsifier, preferably Polysorbate 20.

In these fourth embodiments, the preferred hydrocarbon is polyisobutene, isohexadecane or a white mineral oil.

In some fourth embodiments, the thickening/gelling agent contains at least one emulsifier of water-in-oil (W/O) type and/or at least one emulsifier of oil-in-water (O/W) type, in the form of a reverse latex comprising about 20% to about 70% by weight, and preferably about 25% to about 40% by weight, of a crosslinked anionic polyelectrolyte, the anionic polyelectrolyte being based on partially neutralized acrylic acid, characterized in that the crosslinking agent is chosen from compounds comprising at least two allyl radicals and most particularly from diallyloxyacetic, sodium diallyloxyacetate or triallylamine.

In some other fourth embodiments, the thickening/gelling agent contains at least one emulsifier of water-in-oil (W/O) type and at least one emulsifier of oil-in-water (O/W) type, in the form of a reverse latex comprising about 20% to about 70% by weight, and preferably about 25% to about 40% by weight, of an anionic polyelectrolyte which may be branched and/or crosslinked, wherein the anionic polyelectrolyte is based on partially neutralized acrylic acid, in the form of an amino alcohol salt, and preferably a monoethanolamine salt.

Processes for making these agents are disclosed in U.S. Pat. No. 6,346,239. A suitable process entails:

a) an aqueous solution containing the monomers and the optional additives is emulsified in an oil phase in the presence of one or more emulsifiers of water-in-oil type;

b) the polymerization reaction is initiated by introducing a free-radical initiator and optionally a co-initiator into the emulsion formed in a), after which the reaction is left to proceed; and c) when the polymerization reaction is complete, one or more emulsifiers of oil-in-water type are introduced at a temperature below 50° C.

According to one variant of this process, the reaction medium obtained from step b) is concentrated by distillation before step c) is carried out. According to a preferred embodiment, the polymerization reaction is initiated by a redox couple which generates hydrogen sulphite ions ($HSO_3^-$), such as the cumene hydroperoxide/sodium metabisulphite ($Na_2S_2O_5$) couple the sodium, potassium or ammonium peroxydisulphate/sodium metabisulphite or the cumene hydroperoxide/thionyl chloride ($SOCl_2$) couple, at a temperature below or equal to 10° C., if desired accompanied by a polymerization co-initiator such as, for example, azobis(isobutyronitrile), followed by proceeding either under virtually adiabatic conditions up to a temperature of greater than or equal to 50° C., or by controlling the temperature.

In preferred embodiments, the thickening/gelling contains Polysorbate 20 and polyisobutene. Such a product is commercially available from SEPPIC under the tradename Sepiplus 400.

In the polymeric constituent of the fifth embodiment, the strong acid functional group of the monomer containing it is in particular the sulphonic acid functional group or the phosphoric acid functional group, partially or completely salified. The monomer may be for example partially or completely salified styrene sulphonic acid or preferably partially or completely salified 2-methyl-2-[(1-oxo-2-propenyl-)amino]-1-propanesulphonic acid, in particular in the form either of an alkali metal salt such as for example the sodium salt or the potassium salt, or of an ammonium salt, or the salt of an amino alcohol such as for example the monoethanolamine salt or the salt of an amino acid such as for example the lysine salt.

The weak acid functional group of the monomer containing it is in particular the carboxylic acid functional group, and preferably the monomer is chosen from acrylic acid, methacrylic acid, itaconic acid, maleic acid or 3-methyl-3-[(1-oxo-2-propenyl)amino]butanoic acid, the acids being partially or completely salified, in particular in the form either of an alkali metal salt such as for example the sodium salt or the potassium salt, or of an ammonium salt, or the salt of an amino alcohol such as for example the monoethanolamine salt or the salt of an amino acid such as for example the lysine salt.

The neutral monomer is chosen in particular from acrylamide, methacrylamide, dimethyl acrylamide, (2-hydroxyethyl)acrylate, (2,3-dihydroxypropyl)acrylate, (2-hydroxyethyl)methacrylate, (2,3-dihydroxypropyl)methacrylate, diacetone acrylamide or an ethoxylated derivative, having a molecular weight of between 400 and 1000, of each of these esters.

Specific examples of the anionic polyelectrolyte of these fifth embodiments include the following polymers: a) copolymer of acrylic acid partially salified in the form of an alkali metal salt or of an ammonium salt and of acrylamide, crosslinked with methylenebis(acrylamide); b) copolymer of 2-methyl-2-[(1-oxo-2-propenyl)amino]-1-propanesulphonic acid partially salified in the form of an alkali metal salt or of an ammonium salt and of acrylamide, crosslinked with methylenebis(acrylamide); c) copolymer of 2-methyl-2-[(1-oxo-2-propenyl)amino]-1-propanesulphonic acid partially salified in the form of a sodium salt and of acrylic acid partially salified in the form of an alkali metal salt or of an ammonium salt, crosslinked with methylenebis-(acrylamide); d) copolymer of 2-methyl-2-[(1-oxo-2-propenyl)amino]-1-propanesulphonic acid partially salified in the form of an alkali metal salt or of an ammonium salt and of 2-hydroxyethyl acrylate, crosslinked with methylenebis(acrylamide); e) homopolymer of 2-methyl-2-[(1-oxo-2-propenyl)amino]-1-propanesulphonic acid partially salified in the form of an alkali metal salt or of an ammonium salt, crosslinked with methylenebis (acrylamide); f) homopolymer of acrylic acid partially salified in the form of an ammonium salt or of a monoethanolamine salt, crosslinked with sodium diallyloxyacetate; and g) a homopolymer of acrylic acid partially salified in the form of an ammonium salt or of a monoethanolamine salt, crosslinked with triallylamine.

These agents, including methods for making them, are disclosed in U.S. Patent Publication 2005/0002977. A preferred fifth embodiment is commercially available from SEPPIC under the name SEPINOV EMT-10 (INCI name: hydroxyethyl acrylate/sodium acryloyldimethyl taurate copolymer). These agents may be in the form of a powder.

The thickening/gelling agents generally contain between 20% and 50% water, at least insofar as the first, second, third and fourth embodiments are concerned. In the fifth embodiments, the amount of water is up to about 19% water, e.g., at least about 0.5% or at least about 2% by weight of the agent. The agents can also contain various additives such as complexing agents, transfer agents, wetting agents and/or chain-limiting agents.

The thickening/gelling agents of the present invention are generally present in the cosmetic compositions in amounts ranging from about 0.1% to 15%, and preferably from about 0.5% and 5%, by weight of the composition.

Derivatives of hydrocortisone include esters e.g., mono- and di-esters, such as hydrocortisone 21-acetate; hydrocortisone 21-benzadac; hydrocortisone 21-cyclopentylpropionate; hydrocortisone 21-hemisuccinate; hydrocortisone 21-acetate 17-propionate; hydrocortisone 17-butyrate; hydrocortisone 17-valerate; and hydrocortisone 17-butyrate 21-propionate; and salts thereof.

The amount of hydrocortisone (or derivative thereof) in the compositions according to the present invention is generally not greater than about 10% (e.g., about 0.1 to about 10% by weight). Preferably, the hydrocortisone is present in the compositions of the present invention in an amount between 0.01 and 5% by weight, and more particularly between 0.2 and 4%, based on the total weight of the composition. These amounts are effective to treat conditions for which hydrocortisone and its salts and esters are indicated, e.g., eczema, atopic dermatitis, psoriatic or eczematous erythrodermy, pruriginous lesions, chronic erythematous lupus, patch psoriasis and parapsoriasis, hyperthrophic cicatrix, and radiotherapic or solar erythema. Frequency and amount of use of the compositions of the present invention will depend upon numerous factors, including the condition being treated and its severity. For example, application of compositions containing hydrocortisone e.g., to treat one of the conditions disclosed above, typically requires an application of the composition of the present invention to the affected area of the skin, on the average, twice each day, optionally with a massaging action in order to facilitate the penetration thereof into the skin.

At least one glycol is present in the compositions of the present invention. Glycols include propylene glycol, butylene glycol, pentylene glycol and hexylene glycol. Applicants have found that the solubility of hydrocortisone in pentylene glycol is about 6%, which is higher than the solubility of hydrocortisone in other glycols. Thus, pentylene glycol is preferred. In some embodiments, more than one glycol is present. Total amount of glycols generally ranges from about 10% to about 99% by weight of the composition. Pentylene glycol is typically present in an amount of about 5% to about 50%, and when present with at least one other glycol, about 7% to about 10% by weight of the composition. Amounts of other glycols also ranges from about 5% to about 50%, and when present with pentylene glycol, about 10% to about 20% by weight of the composition. Other solvents (or "co-solvents"), particularly non-volatile solvents, may be present in the composition. These solvents include esters and other polyols such as glycerin, polyethylene glycols, polypropylene glycols, and mixtures thereof.

The compositions according to the present invention can be provided in various forms, principally in the form of emulsions (e.g., creams), gels, lotions and shampoos. They may also be in anhydrous form e.g., in the form of an ointment, gel or pomade. Emulsions and gels are preferred. Compositions of the present invention other than those in anhydrous form have an aqueous phase and an oil or fatty phase. When the composition according to the invention is an emulsion, the proportion of the fatty phase generally ranges from about 0.5% to about 80% by weight and preferably from about 5% to about 50% by weight, based on the total weight of the composition. Oils, waxes, emulsifiers and co-emulsifiers that are typically present in the composition may be selected from those conventionally used in cosmetics and dermatology.

The fatty phase oroily phase usually contains at least one oil. Examples include hydrocarbon-based oils of animal origin, such as perhydrosqualene; hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, jojoba oil or karite butter oil; synthetic esters and synthetic ethers, especially of fatty acids, for instance oils of formulae $R^6COOR^7$ and $R^6OR^7$, in which $R^6$ represents a fatty acid residue containing from 8 to 29 carbon atoms, and $R^7$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyl-dodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate; linear or branched hydrocarbons of mineral or synthetic origin, such as volatile or non-volatile liquid paraffins, and derivatives thereof, petroleum jelly, polydecenes, and hydrogenated polyisobutene such as Parleam oil; fatty alcohols containing from 8 to 26 carbon atoms, such as cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol; alkoxylated and ethoxylated fatty alcohols such as oleth-12; partially hydrocarbon-based and/or silicone-based fluoro oils such as perfluoromethylcyclopentane, perfluoro-1,3-dimethylcyclohexane, perfluoro-1,2-dimethylcyclobutane; perfluoroalkanes such as dodecafluoropentane and tetradecafluorohexane, bromoperfluorooctyl; nonafluoromethoxybutane and nonafluoro-ethoxyisobutane; perfluoromorpholine derivatives, such as 4-trifluoromethylperfluoromorpholine; silicone oils such as volatile or non-volatile polymethylsiloxanes (PDMSs) containing a linear or cyclic silicone chain, and that are liquid or pasty at room temperature, e.g., cyclopolydimethylsiloxanes (cyclomethicones) such as cyclohexa-siloxane; polydimethylsiloxanes comprising alkyl, alkoxy or phenyl groups, that are pendent or at the end of a silicone chain, these groups containing from 2 to 24 carbon atoms; phenylsilicones, such as phenyltrimethicones, phenyldimethicones, phenyltrimethylsiloxydiphenylsiloxanes, diphenyldimethicones, diphenylmethyldiphenyltrisiloxanes, 2-phenylethyl-trimethylsiloxysilicates and polymethylphenylsiloxanes; and mixtures thereof.

Other fatty substances that may be present in the oily phase are, for example, fatty acids containing from 8 to 30 carbon atoms, such as stearic acid, lauric acid, palmitic acid and oleic acid; waxes of animal origin, such as lanolin, beeswax, spermaceti or lanolin derivatives, such as lanolin alcohols, hydrogenated, hydroxylated or acetylated lanolin, lanolin fatty acids and acetylated lanolin alcohol; waxes of vegetable origin, such as camauba, candelilla, kapok, ouricury, rice, hydrogenated jojoba, esparto or japan wax or cork fibre or sugar cane waxes or cocoa butter; mineral waxes, for example paraffin, montan, lignite or petrolatum waxes or microcrystalline waxes, ceresin or ozokerite; or synthetic waxes, such as polyethylene waxes, waxes obtained by the Fischer-Tropsch synthesis and linear esters resulting from the reaction of a saturated $C_{10}$ to $C_{40}$ carboxylic acid and of a saturated $C_{10}$ to $C_{40}$ alcohol, such as myristyl myristate. Use may also be made of cetyl alcohol, stearyl alcohol, calcium lanolates or stearates, castor oil, palm oil, coconut oil, sunflower oil or hydrogenated coconut oil; gums such as silicone gums (dimethiconol); silicone resins such as trifluoromethyl-C1-4-alkyldimethicone and trifluoropropyldimethicone; and silicone elastomers. These fatty substances may be chosen in a varied manner to prepare a composition having the desired properties, e.g., consistency or texture.

The compositions may contain at least one emulsifier (i.e., surfactant) e.g., amphoteric, anionic, cationic and nonionic emulsifiers, used alone or as a mixture. Choice of emulsifier depends upon the nature of the emulsion e.g., water-in-oil (W/O) or oil-in-water (O/W) emulsions. Examples of emulsifiers that may be used in O/W emulsions include nonionic emulsifiers such as saccharide esters and ethers such as sucrose stearate, sucrose cocoate (and mixtures of sucrose stearate and cocoate); polyol esters, in particular glycerol or sorbitol esters, such as glyceryl stearate, polyglyceryl-2 stearate and sorbitan stearate; glycerol ethers; oxyethylenated and/or oxypropylenated ethers such as the oxyethylenated, oxypropylenated ether of lauryl alcohol containing 25 oxyethylene groups and 25 oxypropylene groups (CTFA name "PPG-25 laureth-25") and the oxyethylenated ether of the mixture of $C_{12}$-$C_{15}$ fatty alcohols containing 7 oxyethylene groups (CTFA name "$C_{12}$-$C_{15}$ Paneth-7"); ethylene glycol polymers such as PEG-100, and mixtures thereof.

Examples of emulsifiers for use in W/O emulsions include fatty esters of a polyol, in particular of glycerol or of sorbitol, and in particular polyol isostearates, oleates and ricinoleates; saccharide esters and ethers such as methyl glucose dioleate; fatty esters such as magnesium lanolate; dimethicone copolyols and alkyldimethicone copolyols.

Additional examples of surfactants (emulsifying and coemulsifying) include the esters of fatty acids and polyethylene glycol (PEG), esters of fatty acids and glycerol (glyceryl stearate) or esters of fatty acids and sugar (sorbitan stearate), as well as the polyoxyethylenated or polyoxypropylenated derivatives thereof, cyclomethicones and dimethicone copolyols, and also anionic surfactants (e.g., potassium or sodium alkyl phosphates).

Lotions generally contain the active agent e.g., hydrocortisone or salt or ester thereof, solubilized in one or more glycols, optionally with one or more additional solvents. The ointments are anhydrous compositions based, for example, on petrolatum, paraffin oil or waxes.

Other cosmetically or dermatologically acceptable agents that may be used in the compositions of the invention include coloring agents (pigments, dyes, colorants e.g., iron oxides, titanium oxides and zinc oxides), preservatives, perfumes and fragrances, hydrating active agents, ultraviolet ray-absorbing agents (sunscreen or sunblock agents), pulverulent agents, antiperspirants and/or odor absorbers, moisturizers, for example protein hydrolysates and polyols such as glycerol, and sugar derivatives; natural extracts; procyannidol oligomers; vitamins, for instance vitamin A (retinol), vitamin C (ascorbic acid), vitamin E (tocopherol), vitamin B5 (panthenol) and vitamin B3 (niacinamide); vitamin K; urea; caffeine; depigmenting agents such as kojic acid and caffeic acid; salicylic acid; alpha-hydroxy acids such as lactic acid and glycolic acid; retinoids such as carotenoids; fillers, keratolytic agents, anti-oxidants, melatonin; extracts of algae, fungi, plants, yeasts or bacteria; hydrolysed, partially hydrolysed or unhydrolysed proteins, and enzymes; antibacterial or bactericidal agents e.g., 2,4,4'-trichloro-2'-hydroxydiphenyl ether (triclosan) and 3,4,4'-trichlorocarbanilide (or triclocarban), azelaic acid and benzoylperoxide; matt-effect agents, for instance fibers; tensioning agents; optical brighteners; and mixtures thereof, as well as additional active ingredients aside from the active agents of the present invention. Amounts of such agents typically range from about 0.0001% to about 20% by weight of the composition. For example, U.S. Pat. No. 5,643,898 teaches a combination for inducing and stimulating hair growth, or decreasing hair loss, containing hydrocortisone and a pyrimidine derivative, e.g., Minoxidil. Thus, persons skilled in the art will be able to select additional active ingredients and inert ingredients suitable for administration to skin or scalp as desired. See, e.g., U.S. Pat. No. 5,275,755 (directed to shampoo compositions).

The following examples are intended to further illustrate certain embodiments of the invention and are not intended to limit the invention in any way. Unless otherwise indicated, all percentages are weight-by-weight.

EXAMPLES

Example 1

Comparative Stability of Hydrocortisone with Various Thickening/Gelling Agents

Stability and cosmetic esthetics/acceptability were evaluated in connection with compositions containing 1% w/w hydrocortisone and 1.0-3% w/w of various thickening/gelling agents, namely Carbopol Ultrez 10, Carbopol 980, Pemulen TR 1, Klucel HF (hydroxypropylcellulose), Natrosol (hydroxyethylcellulose), Sepigel 305, Simugel EG, Simulgel 800, Simulgel 600, Sepiplus 400, sodium acrylate and AMPS. The compositions were prepared by dispersing the gelling agents into the glycol/hydrocortisone. They were placed into containers and stored at 45° C.

To evaluate stability, each composition was analyzed for hydrocortisone with HPLC. The results showed that the compositions containing Klucel HF, Natrosol, Sepigel 305, Simugel EG, Simulgel 800, Simulgel 600 and Sepiplus 400 were stable.

To evaluate cosmetic acceptability, each composition was evaluated for their tack and cosmetic acceptance by chemists. The results showed that the compositions containing Sepigel 305, Simugel EG, Simulgel 800, Simulgel 600 and Sepiplus 400 were cosmetically acceptable.

Example 2

Emulsion

TABLE 3

| Phase | INCI Name (Trade Name) | |
|---|---|---|
| A | Water | 51.800 |
|   | Propylene glycol | 7.000 |
|   | Pentylene glycol | 10.000 |
|   | Butylene glycol | 10.000 |
|   | Preservatives | 0.300 |
|   | Nylon 12 | 2.000 |
|   | Hydrocortisone, USP (Micronized) | 1.000 |
| B | Dicaprylyl ether (Cetiol OE) | 3.000 |
|   | C12-15 Alkyl benzoate | 3.000 |
|   | Octyl palmitate | 3.000 |
|   | Isononyl isononaoate | 1.000 |
|   | Cetyl dimethicone (Abil wax 9801) | 1.000 |
|   | Cetearyl alcohol and Dicetyl phosphate and Ceteth-10 phosphate (Crodafos CES) | 3.600 |
|   | Glyceryl monostearate self-emulsifier | 1.500 |
|   | Preservatives | 0.700 |

TABLE 3-continued

| Phase | INCI Name (Trade Name) | |
|---|---|---|
| C | Polyacrylamide (and) C13-14 isoparaffin (and) laureth-7 (Sepigel 305) | 1.100 |
| | Total | 100.00 |

To prepare the composition described in table 3, the batch amount of water was added to the main beaker. The remaining ingredients of phase A were mixed separately and then added to the main beaker. The ingredients of phase B were added to a separate container and mixed at 50° C. until clear. The mixture was allowed to cool to room temperature, and then was added to the main beaker while mixing. The mixing was continued until homogeneous. The ingredients of phase C were mixed in a separate container, followed by the addition of the mixture of phases A and B thereto, while mixing. The batch was homogenized for 5 minutes.

Example 3

Hydrocortisone Gel

| Phase | INCI Name (Trade Name) | % |
|---|---|---|
| A | Water | 36.00 |
| | Simulgel 600 | 3.00 |
| B | Propylene glycol | 15.00 |
| | Pentylene glycol | 10.00 |
| | Butylene glycol | 35.00 |
| | Hydrocortisone | 1.00 |
| | Total | 100.00 |

To prepare the gel, the batch amount of water was weighed and then added to main beaker. Phase B ingredients were weighed and combined in a separate container, and mixed at 50° C. until clear, followed by cooling to room temperature. Phase B was then added to the main beaker while mixing. Mixing was continued until the resultant solution was homogeneous. Simulgel 600 was added while mixing cold with the homogenizer. Mixing was stopped when the Simulgel was completed hydrated.

Example 4

Hydrocortisone Gel

| Phase | INCI Name (Trade Name) | % |
|---|---|---|
| A | Water | 36.00 |
| | Sepigel 305 | 3.00 |
| B | Propylene glycol | 15.00 |
| | Pentylene glycol | 10.00 |
| | Butylene glycol | 35.00 |
| | Hydrocortisone | 1.00 |
| | Total | 100.00 |

The gel was prepared by the same procedure used to make the gel shown in example 3, except that Sepigel 305 was used as the thickening/gelling agent.

Example 5

Hydrocortisone Gel

| Phase | INCI Name (Trade Name) | % |
|---|---|---|
| A | Water | 37.00 |
| | Sepiplus 400 | 2.00 |
| B | Propylene glycol | 15.00 |
| | Pentylene glycol | 10.00 |
| | Butylene glycol | 35.00 |
| | Hydrocortisone | 1.00 |
| | Total | 100.00 |

The gel was prepared by the same procedure made used to make the gel shown in Example 3, except that Sepiplus 400 was used as the thickening/gelling agent.

Example 6

Hydrocortisone Gel

| Phase | INCI Name (Trade Name) | % |
|---|---|---|
| A | Water | 36.00 |
| | Simulgel EG | 3.00 |
| B | Propylene glycol | 15.00 |
| | Pentylene glycol | 10.00 |
| | Butylene glycol | 35.00 |
| | Hydrocortisone | 1.00 |
| | Total | 100.00 |

The gel was prepared by the same procedure used to make the gel shown in Example 3, except that Simulgel EG was used as the thickening/gelling agent.

Example 7

Hydrocortisone Gel

| Phase | INCI Name (Trade Name) | % |
|---|---|---|
| A | Water | 36.00 |
| | Simulgel 800 | 3.00 |
| B | Propylene glycol | 15.00 |
| | Pentylene glycol | 10.00 |
| | Butylene glycol | 35.00 |
| | Hydrocortisone | 1.00 |
| | Total | 100.00 |

The gel was prepared by the same procedure used to make the gel shown in Example 3, except that Simulgel 800 was used as the thickening/gelling agent.

All publications cited in the specification are indicative of the level of skill of those skilled in the art to which this invention pertains. All these publications are herein incorporated by reference to the same extent as if each individual publication were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition consisting of:
hydrocortisone, or an ester or a salt thereof;
pentylene glycol;
water;
a gelling agent comprising an acrylamide and sodium acrloyldimethyl taurate copolymer, an emulsifier, and an oil;
optionally, propylene glycol or butylene glycol; and
optionally oils other than the oil in the gelling agent, fatty acids, waxes, cetyl alcohol, stearyl alcohol, calcium lanolates or stearates, gums, emulsifiers other than the emulsifier in the gelling agent, surfactants, gelling agents other than the gelling agent comprising an acrylamide and sodium acrloyldimethyl taurate copolymer, coloring agents, preservatives, perfumes, hydrating active agents, moisturizers, vitamins, urea, caffeine, salicylic acid, alpha-hydroxy acids, retinoids, keratoylytic agents, anti-oxidants, antibacterial or bacterial agents, benzoyl peroxide, matt-effect agents, optical brighteners, or mixtures thereof.

2. The composition of claim 1, wherein the emulsifier in the gelling agent is a polyethoxylated sorbitan ester.

3. The composition of claim 2, wherein the emulsifier is polysorbate 80.

4. The composition of claim 1, wherein the oil in the gelling agent is isohexadecane.

5. The composition of claim 1, wherein the composition includes at least one glycol selected from the group consisting of propylene glycol and butylene glycol.

6. The composition of claim 1, wherein the composition includes both propylene glycol and butylene glycol.

7. The composition of claim 1 formulated as a gel.

8. A cosmetic composition consisting of:
hydrocortisone, or an ester or a salt thereof;
pentylene glycol;
a gelling agent comprising an acrylamide and sodium acrloyldimethyl taurate copolymer, a polyethoxylated sorbitan ester, and isohexadecane;
optionally, at least one glycol selected from the group consisting of propylene glycol and butylene glycol; and
optionally oils other than the isohexadecane in the gelling agent, fatty acids, waxes, cetyl alcohol, stearyl alcohol, calcium lanolates or stearates, gums, emulsifiers other than the polyethoxylated sorbitan ester in the gelling agent, surfactants, gelling agents other than the gelling agent comprising an acrylamide and sodium acrloyldimethyl taurate copolymer, coloring agents, preservatives, perfumes, hydrating active agents, moisturizers, vitamins, urea, caffeine, salicylic acid, alpha-hydroxy acids, retinoids, keratoylytic agents, anti-oxidants, antibacterial or bacterial agents, benzoylperoxide, matt-effect agents, optical brighteners, or mixtures thereof.

9. The cosmetic composition of claim 8, wherein the composition includes at least one glycol selected from the group consisting of propylene glycol and butylene glycol.

10. The composition of claim 8, wherein the compositions includes both propylene glycol and butylene glycol.

11. A method for treating the skin comprising applying a composition of claim 1 to the skin.

12. A method for treating eczema, atopic dermatitis, psoriatic or eczematous erythrodermy, pruriginous lesions, chronic erythematous lupus, patch psoriasis, parapsoriasis, hyperthrophic cicatrix, radiotherapic erythema or solar erythema comprising applying to the skin an effective amount of a composition of claim 1 to the skin.

13. The composition of claim 1, wherein the total amount of pentylene glycol present is about 5% to about 50% by weight based on the total weight of the cosmetic composition.

14. The composition of claim 5, wherein the total amount of pentylene glycol is about 7% to about 10% by weight based on the total weight of the cosmetic composition.

15. The composition of claim 5, wherein the total amount of glycols other than pentylene glycol is about 10% to about 20% by weight based on the total weight of the cosmetic composition.

16. The composition of claim 14, wherein the total amount of glycols other than pentylene glycol is about 10% to about 20% by weight based on the total weight of the cosmetic composition.

* * * * *